United States Patent [19]

Roberts et al.

[11] 3,935,306

[45] Jan. 27, 1976

[54] TOOTHPASTE FORMULATIONS

[75] Inventors: Francis D. Roberts, Millinton, N.J.;
John J. Steinke, III, Syracuse, N.Y.

[73] Assignee: Colgate-Palmolive Company, New York, N.Y.

[22] Filed: Feb. 8, 1974

[21] Appl. No.: 440,945

Related U.S. Application Data

[63] Continuation of Ser. No. 243,060, April 11, 1972, abandoned, which is a continuation-in-part of Ser. No. 147,613, May 27, 1971, abandoned, which is a continuation of Ser. No. 749,934, Sept. 5, 1968, abandoned.

[52] U.S. Cl. ............................................. 424/49
[51] Int. Cl.$^2$ ........................................... A61K 7/16
[58] Field of Search .............................. 424/49–58

[56] References Cited
UNITED STATES PATENTS

| | | | |
|---|---|---|---|
| 2,196,154 | 4/1940 | Schulerud | 424/55 |
| 3,538,230 | 11/1970 | Pader et al. | 424/50 |
| 3,574,823 | 4/1971 | Roberts et al. | 424/49 |
| 3,767,791 | 10/1973 | Cordon et al. | 424/49 |
| 3,803,301 | 4/1974 | Cordon et al. | 424/49 |

FOREIGN PATENTS OR APPLICATIONS

| | | | |
|---|---|---|---|
| 2,031,676 | 1/1971 | Germany | 424/49 |

*Primary Examiner*—Shep K. Rose

[57] ABSTRACT

Toothpaste formulations having dispersed therein a plurality of agglomerated particles of dental polishing agent that are visible, palpable and substantially insoluble in the toothpaste are disclosed. The agglomerates comprise individually impalpable particles of water insoluble dental polishing agent; can include an agglomerating agent and are reduced to smaller sized particles of dental polishing agent when subjected to mild mechanical agitation such as toothbrushing. Such agglomerates are particularly well suited for incorporation into transparent gel dental vehicles to provide special effects such as supplemental cleaning and polishing characteristics without adversely affecting the visual clarity of the finished toothpaste.

13 Claims, No Drawings

TOOTHPASTE FORMULATIONS

RELATED APPLICATIONS

This application is a continuation of application Ser. No. 243,060 filed Apr. 11, 1972 (now abandoned) which is in turn a continuation-in-part of application Ser. No. 147,613 filed May 27, 1971 (now abandoned), the latter being in turn a continuation of Ser. No. 749,934 filed Sept. 5, 1968 (now abandoned).

The entire disclosure of our patent no. 3,574,823 issued Apr. 13, 1971 (Ser. No. 750,028 filed Aug. 5, 1968; reissue application Ser. No. 224,629 filed Feb. 8, 1972) is hereby incorporated by reference.

The invention relates to toothpaste formulations containing dispersed therein visible, palpable agglomerated particles of dental polishing agent that are substantially insoluble in the toothpaste and are easily reduced to impalpable particles of dental polishing agent during toothbrushing.

Polishing agents have beem employed in toothpastes in order to facilitate cleansing of the teeth. Since these agents are typically water-insoluble, they have been used in small particle sizes, substantially all of which are typically less than 177 microns in size and often even less than 10 microns. Such small size particles help avoid too much abrasiveness, palpability and retention of individual particles in the oral cavity even after rinsing which would be expected if larger particles of water-insoluble polishing agent were employed. However, these small particles, being individually invisible, could not contribute to the esthetic appearance of the dentifrice. The agglomerated particles of the invention, being visible, contribute markedly to the esthetic appeal of a dentifrice composition by providing a speckled, or dotted appearance when the agglomerated particles contrast with the toothpaste base or matrix. When dispersed in a transparent gel dental matrix, the new agglomerated particles provide a stable unique speckled appearance and desired polishing characteristics. In the clear gel dental base, the agglomerated particles are visible both on the surface and in the interior of the toothpaste; the combination due to the unique light reflectance effects, giving a positive three dimensional sparkling appearance. In an opaque paste, of course, only special portions of the agglomerates on the surface would be visible resulting in an essentially uni-dimensional effect.

In accordance with certain of its specific aspects, this invention utilizes an agglomerated particulate material containing water-insoluble dental polishing agent, particles of said agglomerated material being visible, said agglomerated particles being palpable and substantially water-insoluble, and easily reducible to individual particles of polishing agent, each of which is fine, invisible and impalpable upon being subjected to mild mechanical action. The agglomerated particles maintain their physical integrity until used in toothbrushing i.e., they are substantially insoluble in the toothpaste and do not disintegrate to any appreciable extent when blended with the toothpaste.

Preferably the agglomerated particles of water-insoluble dental polishing agent also contain agglomerating agent having binding and/or lubricating properties, in order to facilitate agglomeration of the polishing agent particles. The agglomerating agent can be water-soluble so that it dissolves in saliva when the particles are broken down by mild mechanical action or it can be a water-insoluble material. The various agglomerating agents mentioned below are typical examples of gums, gels, waxes, polymers etc. which are known as binders or the like in manufacture of tablets and other compressed or agglomerated materials.

Water-insoluble dental polishing agents of the prior art may be used in accordance with this invention. The polishing agents thus include insoluble phosphate salts, such as insoluble sodium metaphosphate, insoluble potassium metaphosphate, calcium pyrophosphate, magnesium orthophosphate, trimagnesium orthophosphate, tricalcium phosphate, dicalcium phosphate dihydrate, anhydrous dicalcium phosphate and the like, calcium carbonate, magnesium carbonate, hydrated alumina, silica, zirconium silicate, aluminum silicate including calcined aluminum silicate and polymethyl methacrylate.

Special effects in appearance and functionality as desired may be obtained by appropriate selection of polishing agents depending upon their hardness, particle size abrasivity etc; in the agglomerates when integrated with the toothpaste base. For example, certain polishing agents will destroy the clarity of a clear toothpaste base but may be utilized in the agglomerates satisfactorily. Hard materials having a Moh hardness of at least 5 and a particle size such as to be useful as a dental polishing agent (e.g. between 0.1 and 10 microns) are particularly suitable for use in the agglomerates. Representative of such hard materials are silica, zirconium silicate, aluminum silicate, calcined aluminum silicate, calcium silicate, silicon carbide, pumice, ilmenite ($FeTiO_3$), $CeO_2$, $Fe_2O_3$ (hematite), $SnO_2$, Topaz (aluminum hydroxy fluoro silicate) and $TiO_2$, either natural or manufactured. When incorporated into a toothpaste, agglomerated particles of hard abrasive materials as defined above e.g. Moh hardness greater than 5, particle size between 0.1 and 10 microns, make it possible to provide substantially increased cleaning and polishing properties to the formulation, without significantly increasing abrasion to the dental hard tissues, (enamel, dentin and cementum).

The insoluble alkali metal metaphosphate polishing agents are preferably the insoluble sodium and potassium salts of polymetaphosphoric acid. These materials are known in the art with the insoluble sodium metaphosphate having been suggested as a polishing agent as previously indicated. Such materials may be formed in any suitable manner, as illustrated by Thorpe's Dictionary of Applied Chemistry, Vol, 9(4th. ed.), pp. 510–511. The forms of insoluble sodium metaphosphate known as Madrell's salts and Kurrol's salt are further examples of suitable materials.

These metaphosphate salts exhibit only a minute solubility in water, and are commonly referred to as insoluble metaphosphate, therefore. There is present a minor amount of soluble phosphate material as impurities, usually of the order of a few percent such as up to about 4% by weight. The amount of soluble phosphate material which is believed to be a soluble sodium trimetaphosphate in the case of insoluble sodium metaphosphate may be reduced by washing with water if desired.

Agglomerating agents which may be employed to assist formation of the polishing agent into agglomerated particles include water-soluble materials such as gum acacia (arabic), gelatin, starches, alkali metal carboxymethyl celluloses, polyethylene glycols, glucose, sucrose, methyl cellulose, carboxymethyl hydroxymethyl celluloses, sodium alginate, polyvinyl pyrrolidone, polyvinyl alcohol, Irish moss, gum tragacanth, magnesium aluminum silicate gel and the like. Other agglomerating agents include materials such as talc, magnesium stearate, calcium stearate, stearic acid and the like which are water-insoluble materials and known as lubricants also.

Mixtures of agglomerating agents may be employed too. When the polishing agents are freed from binding with these agents upon application of mild pressure, typically a toothbrush applied in the oral cavity, these agents are easily solubilized or dispersed in the saliva so as to permit the particles of polishing material to exert desired polishing or cleansing power simultaneously with the balance of the toothpaste.

Typically, the polishing agent may comprise a major proportion e.g., about 75%–100% by weight, preferably about 75%–99%, of the finished agglomerate particles. The agglomerating agent when present typically comprises a sufficient amount to facilitate agglomeration, usually 1%–25% by weight of the finished agglomerate. Lesser amounts such as at least about 10% may be used with an appropriate proportion of suitable agglomerating material so as to provide stable agglomerates of desired properties.

When employed, the agglomerating agent is blended with the polishing agent in any suitable manner. The agglomerating agent may be blended in dry powdered form or in solution in water or alcohol. The agglomerate may be formed in a dry process known as "slugging" or in a wet granulation process or in a combination of the two wherein wet granulated and dried agglomerates are subsequently subjected to the direct compression process as herein after described.

The large tablet thereby formed typically has dimensions of about 6 mm. × 25 mm., although it may be even larger. The tablet is then broken into granular agglomerates that are individually visible to the naked eye having particle sizes up to about 2380 microns, preferably up to about 840 microns, and most preferably between 200 and 500 microns, typically in a mill, granulator or comminutor.

When the dry or slugging process is employed, the blend to be agglomerated preferably includes an agglomerating agent having lubricating properties such as talc, magnesium stearate, calcium stearate, stearic acid, adipic acid and the like. The lubricating properties of the agglomerating agent facilitates agglomeration and it is present in a suitable amount to do this.

When agglomerating agent in dry powdered form is blended with polishing agent in the wet granulation process, solvent, such as water or ethanol or a solution of additional agglomerating agent, is contacted with the blend in sufficient amount to wet the mass.

The wet granulation process may be performed by wetting a powder blend of water-insoluble dental polishing agent particles typically having a particle size of less than 74 microns; and agglomerating agent in continuous contact on a Dravo pan, in a Hobart mixer or other suitable powder-wetting mixing device thereby forming a wet mass. The "wetting" may be performed by contact of the polishing agent with solid binder followed by moistening or with a solution of the binder.

The wet mass formed from the polishing agent and agglomerating agent is forced through a screen having uniform openings which may be up to 2380 microns e.g. from 420 microns, in size as agglomerates and dried typically in air or an oven. The agglomerates may be segregated into desired clearly visible sizes such as from about 200 up to about 840 microns and preferably up to about 500 microns by passing through appropriately sized screens. It is noted that when the wet mass is formed in a Dravo pan, the forced screening may be unnecessary.

It is desirable that the agglomerates formed be easily introduced into the oral cavity in a toothpaste and comfortably maintained there until reduced in size during toothbrushing. Therefore, those agglomerated particles, having a particle size larger than about 2380 microns, may be preferably separated from the agglomerates. In order to maximize the esthetic appearance of the agglomerates when they are incorporated into a toothpaste, it is desirable also to separate fines, which have a particle size smaller than about 420 microns e.g., substantially less than about 200 microns. However, any agglomerates containing the components of the invention which are visible to the naked eye within the scope of the invention.

If desired, the blend to be agglomerated, by wet or dry procedures, may also contain a non-abrasive diluent or filler, such as lactose, starch, mannitol and the like in amounts of about 1%–5% by weight of the agglomerate, in order to ameliorate the polishing power of the agglomerate. Furthermore, the blend may include ancillary components, such as a color dye or pigment. Typical dyes and pigments include water-insoluble FD&C dyes and lakes and the like. Color material when employed, generally is present in amounts of about 1–10% by weight.

The agglomerate is characterized as being substantially insoluble in the toothpaste during storage. In the oral cavity it is quickly reduced in size from the visible, palpable agglomerates introduced into individual, invisible, fine, impalpable particles upon subjection to mild mechanical action, such as by rubbing on the teeth, gums or other portions of the oral cavity with a toothbrush, the tongue, a finger or the like.

The toothpaste formulation contains a dental vehicle which forms a gel or creamy mass of a consistency which can be desirably extruded from a collapsible tube such as an aluminum tube or a lead tube. The vehicle contains liquids and solids. In general, the liquid portion comprises water, glycerine, sorbitol, propylene glycol, polyethylene glycol 400 or the like including suitable mixtures thereof. It is usually advantageous to use a mixture of both water and humectant, such as glycerine, sorbitol, propylene glycol or the like. The total liquid content is generally about 20–89.5%, usually about 20–50% by weight of the toothpaste.

The solid portion of the vehicle includes a gelling agent, such as the natural and synthetic gums and gum-like materials, such as Irish Moss, gum tragacanth, alkali metal carboxymethyl cellulose and hydroxymethyl carboxyethyl cellulose, polyvinyl pyrrolidone, starch, water soluble hydrophilic colloidal carboxyvinyl polymers, such as those sold under the trademark Carbopol 934 and 940. Such solid portion of the vehicle is typically present in an amount up to about 10% by weight of the toothpaste and preferably about 0.5–5% by weight.

The agglomerated particles are blended into the toothpaste in sufficient amount to provide an attractive appearance of discrete particles and desired polishing effects. Typically, they may comprise any suitable amount, up to about 75%, by weight of the finished toothpaste depending on the desired appearance, polishing effects and type of formulation desired.

In addition to the agglomerates the toothpaste may contain the usual water-insoluble polishing material having a particle size typical of that employed in the art, usually less than about 74 microns, which is invisible in the toothpaste base and increases cleaning or polishing power beyond that provided by the agglomerates. The total polishing material, in the toothpaste is typically between about 5–75%, preferably 10–50%, and can be present partly in the agglomerates and partly in the toothpaste base as desired.

When a transparent or translucent gel matrix is employed in accordance with the invention, the polishing material in the toothpaste base must have a refractive index about the same as the gel base, usually between 1.4 to 1.5, particularly 1.44 and 1.47, in order to maintain visual clarity. Representative of such polishing materials are the colloidal silicas such as xerogels sold under the trademark Syloid. Another type is the synthetic alkali metal or alkaline earth metal aluminosilicate complexes. These siliceous materials can have a particle size up to about 40 microns, preferably between 1 and 20 microns. The total polishing agent present in a transparent or translucent toothpaste according to the invention is usually between 5 and 50 percent by weight and is present partly in the gel vehicle and partly in the form of agglomerated particles of polishing agent. Typically, the transparent or translucent gel vehicle contains from about 5 to 20 by weight of such siliceous polishing agent.

The Syloid silicas are generally white powders, which are transparent and colorless in liquids, have a hardness of about 5 on Moh scale and a refractive index of about 1.46. The surface areas, oil absorptions and bulk densities of some of the Syloid silicas which may be used are, respectively, 675 m²/gm 60/lb/100 lb and 39 lb/ft³ for Syloid 63; 320 m²/gm, 200 lb/100 lb and 16 lb/ft³ for Syloid 74; 330 m²/gm, 200 lb/100 lb and 9 lb/ft³ for Syloid 73; and 310 m²/gm, 310 lb/100 lb and 7 lb/ft³ for Syloid 244.

Suitable aluminosilicate complexes are synthetic amorphous complex aluminosilicate salts of alkali metal or alkaline earth metal in which silica is interbonded with alumina and having a refractive index of about 1.44–1.47, said complex salts containing up to about 20% by weight of moisture and up to about 10% by weight of alkali metal or alkaline earth metal oxide. The complex aluminosilicate slat, e.g. a sodium or calcium salt is typically an amorphous powder, alkaline in nature, of a particle size of up to about 40 microns, preferably about 1–20 microns. The typical moisture content, measured by loss on ignition, is about 5–20% by weight of the agent and the typical content of alkali metal oxide, such as sodium oxide or alkaline earth metal oxide, such as calcium oxide, is up to about 10% by weight. Alumina is typically present in amount up to about 10% by weight and silica typically in amount of at least about 70% by weight; typically, the agent has a loose bulk density of up to about 0.2g/cc, preferably about 0.07–0.12g/cc. The complex aluminosilicate salt appears to contain interbonded silica and alumina having Al-O-Si bonds as described by Tamele, "Chemistry of the Surface and the Activity of Alumina-Silica Cracking Catalyst", *Discussions of the Faraday Society*, No. 8, pages 270–279 (1950) and particularly at Page 273, FIG. 1, Curve 3 wherein the interaction between silica and aluminium ions is potentiometrically detected. Further literature describing this type of complex includes Milliken et al, "The Chemical Characteristics and Structure of Cracking Catalysts", *Discussions of the Faraday Society*, No. 8, Pages 279–290 (1950) and particularly the sentence bridging Pages 284–285. See also Plank et al, "Differences Between Silica and Silica-Alumina Gels I. Factors Affecting The Porous Structure of These Gels", *Journal of Colloid Science*, 2, Pages 399–412 (1947) and Plank, "Differences Between Silica and Silica-Alumina Gels II. A Proposed Mechanism for the Gelation and Syneresis of These Gels," *Journal of Colloid Science* 2, Pages 413–427, (1947) in which formation of the Al-O-Si bond is described at Pages 419–422.

Examples of aluminosilicate complexes are the materials sold by Crosfield as Alusil ET and Alusil N, both of which are amorphous to X-rays and whose typical properties (taken from the manufacturer's publications) are given below:

| | ALUSIL ET | ALUSIL N |
|---|---|---|
| Ultimate particle size (electron microscope) | 20 mµ | |
| Average particle agglomerate size (Coulter Counter) | 6.5±2 | |
| Particle size of agglomerates (sedimentation) | | 98% 30µ |
| Residue on 350 B.S. Sieve (B.S. 1795) | Trace | |
| Oil absorption value (B.S. 1795) | 140±15% w/w | 175% w/w |
| Refractive index | 1.47 | 1.45 |
| Specific gravity | 2.1 | 2.1 |
| Colour (Hunter Reflectometer) (B.S. 1795) | 96+ | |
| pH of a 10% aqueous suspension | 10.5 | 10.5 |
| Loss on drying at 105°C. | 10% | 10% |
| Loss at 1000°C. | 18% | 18% |
| Mol. ratio $SiO_2:Al_2O_3$ (approx.) | 7:1 | 7:1 |
| $SiO_2$ (anhydrous basis) | 78.0% | |
| CaO (anhydrous basis) | — | |
| $Al_2O_3$ (anhydrous basis) | 8.0% | |
| $Na_2O$ (anhydrous basis) | 10.0% | |
| Sulphate and chloride (max.) | 3.0% | |

Another suitable commerically available aluminosilicate complex (also amorphous to X-rays) has the following characteristics): 72% $SiO_2$: 8% $Al_2O_3$; 7% $Na_2O$; 0.05% $Fe_2O_3$; about 6% loss on ignition at 1000°C (including loss of water at 105°C); average primary particle size 35 mu; specific gravity 1.95 g/cm³; refractive index 1.46.

The toothpaste according to the invention may also contain surface-active agent. It is preferred that the total amount of surface-active agent, be about 0.05%–5% by weight, peferably about 1–3%, of the toothpaste. Surface-active agent may include water-soluble sulfates of compounds having long chain alkyl radicals (e.g., chains of 10 to 18 carbon atoms) are suitable. One preferred material is a long chain fatty acid monoglyceride sulfate, such as the sodium salt of hydrogenated coco fatty acid monoglyceride sulfate used alone or in combination with sodium lauryl sulfate. Other suitable materials are the fatty acid amides of amino acids such as sodium N-lauroyl sarcosinate.

Various other materials may be incorporated in the toothpaste. Examples thereof are coloring or whitening agents, preservatives, silicones, fluorine compounds chlorophyll compounds, ammoniated materials, such as urea, diammoniumphosphate and mixtures thereof, antibacterial agents and suitable flavoring and coloring ingredients. Each of these adjuvants may be typically incorporated in the instant toothpaste in amounts up to about 5%. Where coloring is employed, the agglomerates may be colored with a suitable contrasting color. The agglomerates can be colored by including therein a suitable amount, typically from 1 to 10 percent by weight of FD&C dye or lake.

The toothpaste of the invention is formulated by preparing a toothpaste containing no agglomerates and separately preparing the agglomerates in any suitable way. Thus, a gelling agent such as sodium carboxymethyl cellulose or Carbopol 934 and a preservative such as sodium benzoate and polishing material, if employed, is dispersed with a humectant such as glycerin. Water may also be present. Additional humectant and water, as a 70% sorbitol solution, may then be mixed with the dispersion and heat is applied at about 40°–65°C., say 50°C. to form a gel. Surface-active agent, such as sodium lauryl sulfate, if employed, is then dispersed in the mixture. The preparation is then dearated and cooled. Desired flavor may then be added and the toothpaste again dearated.

The agglomerates are then dispersed in the toothpaste with minimal mechanical agitation, insufficient to break them down to a significant degree. The toothpaste, including agglomerated particles of polishing agent, is then deaerated and tubed.

In the following illustrative specific examples, the amounts and proportions of compositions described in these examples are by weight unless otherwise specified.

EXAMPLE I 220 parts of dicalcium phosphate dihydrated having an average particle size of about 4.2 microns are moistened with 91 parts of 10% aqueous solution of gum acacia while blending the components in a Hobart mixer to uniformly wet the blend. The wet mass thereby formed is forced through a screen having uniform openings of 2380 microns and oven dried for one hour at 65°C. The dried agglomerates are then screened through a screen having uniform openings of 420 microns. 132 parts of agglomerated dicalcium phosphate dihydrate are retained on the screen having uniform openings of 840 microns and 37 parts pass through to the screen having uniform openings of 420 microns.

Similar agglomerates of water-insoluble dental polishing agents are made by blending hydrated alumina having an average particle size of about 2.5 microns; zirconium silicate having a mean particle size of about 1 micron; calcium carbonate having particles substantially all of which are less than about 7.4 microns in size; anhydrous dicalcium phosphate having particles substantially all of which are less than about 7.4 microns in size; and insoluble sodium metaphosphate having an average particle size of about 4.8 microns with a 10% aqueous solution of gum acacia.

The agglomerated particles are easily reduced to fine size upon application of mild pressure. Upon incorporation into a toothpaste they are esthetically pleasing. In the oral cavity they are palpable until broken down.

EXAMPLE II 6000 parts of anhydrous dicalcium phosphate particles having sizes indicated in Example I are blended with 150 parts of gum arabic powder and 50 parts of gum tragacanth. The blend is then moistened with a 10% aqueous solution of gum arabic. The agglomerates are then formed and screened in the manner set forth in Example I.

Similar agglomerates may be formed when the blend is moistened with (A) a 20% aqueous solution of gum arabic, (B) a 10% solution of polyvinyl pyrrolidone, (C) water, (D) ethanol or (E) glucose solution.

The agglomerate particles are easily reduced to fine size upon application of mild pressure. Upon incorporation into a toothpaste they are esthetically pleasing. In the oral cavity they are palpable until broken down.

EXAMPLE III

Agglomerates indicated below are made by blending polishing agent, binder and lubricant to form a powder blend. The powder blend is compressed on a rotary tablet press to form slugs about 6 mm. × 25 mm. in size. The slugs are then granulated in an oscillating granulator to form smaller particles. These particles are screened with screens having uniformly spaced openings of 840 microns and 420 microns. 116 parts have particle sizes greater than 840 microns and 266 parts have particle sizes between 420 microns and 840 microns. The remaining agglomerates are finer than 420 microns.

Agglomerates are made by slugging blends of the following components:

| Polishing Agent | (A) | (B) | (C) | Parts (D) | (E) | (F) | (G) | (H) | (I) | (J) | (K) |
| --- | --- | --- | --- | --- | --- | --- | --- | --- | --- | --- | --- |
| Dicalcium Phosphate Dihydrate | 890 | | | | | | | 910 | | | |
| Calcium Carbonate | | 440 | | | | | 865 | | | | |
| Insoluble Sodium Metaphosphate | | 450 | | | 865 | 865 | | | | 900 | |
| Hydrated Alumina | | | 890 | 790 | | | | | 890 | | |
| Zirconium Silicate | | | | | | | | | | | 400 |
| Binder Polyethylene Glycol 6000 | 100 | 100 | 100 | 200 | 100 | 100 | 100 | 130 | 100 | 100 | 100 |
| Lubricant Magnesium Stearate | 10 | 10 | 10 | 10 | | | | 10 | 10 | | |
| Talc | | | | | 35 | 35 | 35 | | | | |
| Stearic Acid | | | | | | 5 | | | | | |

The agglomerate particles are easily reduced to fine size upon application of mild pressure. Upon incorporation into a toothpaste they are esthetically pleasing. In the oral cavity they are palpable until broken down.

EXAMPLE IV 99 parts of unmilled dicalcium phosphate dihydrate having an average particle size of about 118 ± 33 microns are blended with 1 part of magnesium stearate lubricant. The powder blend is compressed on a rotary tablet press to form agglomerate slugs 6 mm. × 25 mm. in size. The slugs are then granulated in an oscillating granulator to form smaller agglomerate particles. These particles are screened with screens having uniformly spaced openings of 840 microns and 420 microns. The agglomerate particles whch pass through the screen with the wider oepnings and are retained on the screen with the narrower openings are separated for incorporation into a toothpaste.

The agglomerate particles are easily reduced to fine size upon application of mild pressure. Upon incorporation into a toothpaste they are esthetically pleasing. In the oral cavity they are palpable until broken down.

EXAMPLE V 20 parts of each of the agglomerate particles described in Example III (A) – (J) are blended with 80 parts of a transparent dental gel vehicle having the following formulation:

|  | Percent |
|---|---|
| Glycerine | 10.00 |
| Sorbitol solution (70%) | 75.00 |
| Sodium benzoate | 0.50 |
| Sodium carboxymethyl cellulose | 2.00 |
| Sodium lauryl sulfate | 1.50 |
| Flavor | 0.80 |
| Ethanol (95%) | 10.00 |
| Color (Red) | 0.10 |

The toothpaste described in this example are transparent and esthetically pleasing. Discrete agglomerated particles including dental polishing agents are randomly dispersed in the finished toothpastes creating an attractive speckled appearance. During toothbrushing the agglomerates are at first palpable and are then easily reduced to individual particles of polishing agent of the fine size upon application of mild pressure with the toothbrush.

EXAMPLE VI 2 parts by weight of the zirconium silicate agglomerated particles of Example III (K) having a particle size between 250 and 420 microns are randomly dispersed in the transparent gel vehicle of Example V. The resulting finished toothpaste has an esthetically attractive speckled appearance comprising whitish speckles in a red clear gel. The whitish speckles are visible both on the surface of the finished toothpaste and internally. Upon brushing the agglomerates are reduced to impalpable particles that are easily removed from the mouth during rinsing.

EXAMPLE VII

Agglomerates having the following composition are prepared in accordance with the wet granulation process of the invention:

|  | Parts |
|---|---|
| Dicalcium phosphate (anhydrous) | 44.95 |
| Dicalcium phosphate dihydrate | 44.95 |
| Polyethylene glycol 6000 | 10.00 |
| Gum arabic | 0.10 |

The agglomerated mass is ground and screened between No. 20 and 40 mesh (U.S. sieve series) resulting in agglomerate particles having a mean size of between 420 and 840 microns. 2 parts by weight of the foregoing discrete agglomerated particles are dispersed in a transparent gel vehicle having the following formulation:

| Component | Parts |
|---|---|
| Glycerine | 25.00 |
| Colloidal silica xerogel (Syloid 74) | 18.00 |
| Colloidal silica xerogel (Syloid 244) | 4.00 |
| Sodium saccharin | 0.17 |
| Sodium benzoate | 0.50 |
| Aqueous 35% solution of Sodium N-lauroyl sarcosinate | 5.70 |
| Sodium carboxymethyl cellulose | 0.35 |
| Sodium fluoride | 0.22 |
| Flavor | 1.00 |
| Color (blue) | 0.08 |
| Aqueous 70% sorbitol solution | 42.98 |
| Chloroform | 2.00 |

The finished toothpaste is a white-speckled blue-clear gel. The white agglomerated particles in the paste easily break down during tooth brushing and are easily rinsed from the mouth. Because of the transparent nature of the finished toothpaste, all of the agglomerated particles are visible.

EXAMPLE VIII

Example VII is repeated using 1 part by weight of the agglomerated particles of Example VII. The finished toothpaste has a speckled appearance although not as pronounced as that of Example VII.

EXAMPLE IX 2 parts by weight of the zirconium silicate agglomerated particles of Example 1 are randomly dispersed in the visually clear gel vehicle of Example VII. The resulting speckled clear gel toothpaste is esthetically attractive. The agglomerated particles are readily disingegrated during toothbrushing.

EXAMPLE X 12 parts by weight of visible white particles of agglomerated anhydrous dicalcium phosphate are mixed with a transparent blue gel vehicle having the following formulation:

| Component | Parts |
|---|---|
| Glycerine | 8.0 |
| Colloidal silica xerogel (Syloid 244) | 8.0 |
| Sodium saccharin | 0.2 |
| Sodium benzoate | 0.4 |
| Sodium lauryl sulfate | 1.2 |
| Sodium carboxymethyl cellulose | 1.6 |
| Flavor | 1.0 |
| Color (F.D. & C. Blue) | 0.8 |
| Aqueous 70% sorbitol solution | 59.0 |
| Ethanol (U.S.P. 190 proof) | 7.8 |

The resulting toothpaste is a white-speckled blue clear gel. The white speckles of agglomerated dicalcium phosphate easily break down during brushing and are easily rinsed from the mouth.

The dicalcium phosphate agglomerates contain about 2% gum acacia as a binder.

Example XI
The following formulations are agglomerated:

| | | Parts |
|---|---|---|
| 1. | Dicalcium phosphate dihydrate | 52.5 |
| | Sodium saccharin | 0.4 |
| | Gum tragacanth | 0.1 |
| 2. | Dicalcium phosphate dihydrate | 52.50 |
| | Sodium saccharin | 0.04 |
| | Sodium alginate | 0.04 |
| 3. | Calcium carbonate | 53.50 |
| | Sodium saccharin | 0.04 |
| | Gum tragacanth | 0.10 |
| 3A. | Calcium carbonate | 53.50 |
| | Sodium saccharin | 0.04 |
| | Gum tragacanth | 2.00 |
| 4. | Anhydrous dicalcium phosphate | 47.75 |
| | Dicalcium phosphate dihydrate | 42.75 |
| | Gum acacia | 0.10 |
| | Powdered polyethylene glycol 6000 | 10.00 |
| 4A. | Anhydrous dicalcium phosphate | 52.25 |
| | Dicalcium phosphate dihydrate | 47.25 |
| | Gum acacia | 0.50 |
| 5. | Anhydrous dicalcium phosphate | 47.45 |
| | Dicalcium phosphate dihydrate | 42.45 |
| | Gum acacia | 0.10 |
| | Polyethylene glycol 6000 | 10.00 |

Formulations 1 to 4A are agglomerated by blending polishing agent, binder and saccharin in a V-shell blender; wetting the blended powder with water in an N-50 Hobart mixer to be able to form balls of the wetted powder; drying the wetted powder overnight in a hot-air tray dryer; sizing granules through a No. 14 screen using a Eureka oscillating granulator and sieving particles using a Cenco-Meinzer shaker to obtain granules which pass through a No. 14 sieve and are retained on a No. 40 sieve.

Formulation 5 is agglomerated by blending a dry powder of the components in a V-shell blender; slugging the powders on a rotary tablet press using maximum pressure on one inch flatfaced punches; breaking large tablets of the slug by forcing them through a Stokes oscillating granulator; and sieveing particles to obtain granules which pass through a No. 14 sieve and are retained on a No. 40 sieve.

50 grams of each of these formulations is incorporated in 500 grams of a clear gel toothpaste vehicle by mixing in an N-50 Hobart laboratory mixer. The vehicle has the following formulation:

| | |
|---|---|
| Glycerine | 25.00% |
| Sorbitol (70% aqueous solution) | 39.55% |
| Sodium benzoate | 0.50% |
| Sodium saccharin | 0.17% |
| Sodium fluoride | 0.22% |
| Sodium carboxymethyl cellulose | 0.35% |
| Syloid 244 (colloidal silicic anhydride) | 3.75% |
| Syloid 74 (colloidal silicic anhydride) | 18.00% |
| Deionized water | 7.60% |
| Chloroform and flavor | 2.50% |
| Sodium lauryl sulfate | 20.00% |
| Color | 0.36% |

In each case the resulting toothpaste is a white-speckled blue clear gel.

In each of the formulations of Example XI the visible agglomerated particles are white and the toothpaste has a white-speckled appearance with all of the speckles being visible. As mentioned earlier, however, the speckles may contain color material such as pigments (e.g. F. D. and C. lakes), in which case the speckles are correspondingly colored.

Example XII
The following opaque toothpaste is prepared:

| | Percent |
|---|---|
| Glycerine (99.3%) | 19.950 |
| Sodium carboxymethyl cellulose | 0.850 |
| Sodium saccharin | 0.200 |
| Sodium benzoate | 0.500 |
| Tetrasodium pyrophosphate | 0.250 |
| Water | 19.986 |
| Trimagnesium phosphate | 0.200 |
| Calcium carbonate | 5.000 |
| Dicalcium phosphate dihydrate | 46.550 |
| Sodium N-lauroyl sarcosinate (35%) | 5.714 |
| Flavor | 0.800 |

200 parts of anhydrous dicalcium phosphate particles having sizes substantially all of which are less than about 7.4 microns and 1 part of D&C Lake Red. No. 30 color, are moistened with 40 parts of a 10% aqueous solution of gum acacia in a Hobart mixer for 10 minutes. The dyed wet mass thereby formed is forced through a screen having uniform openings of 840 microns onto a screen having uniform openings of 420 microns.

10 parts of the dyed agglomerate particles which pass through the screen having uniform openings of 840 microns and which are retained on the screen having uniform openings of 420 microns are blended with 90 parts of the foregoing opaque toothpaste.

The opaque toothpaste described in this example has visible particles of the agglomerates distributed over its surface. During toothbrushing the agglomerated particles are at first palpable and are then easily reduced to individual particles of polishing agent of fine size upon application of mild pressure with the toothbrush.

Although this invention has been described with reference to specific embodiments it will be apparent to one skilled in the art that various modifications may be made thereto without departing from the scope thereof, which is defined by the following claims.

We claim:

1. A speckled toothpaste comprising a translucent or transparent gel toothpaste vehicle having a refractive index between 1.4 and 1.5 and having dispersed therein up to 75% by weight of macroscopically visible, substantially water-insoluble palpable agglomerates of impalpable dental polishing agent particles, said agglomerates having a particle size less than 840 microns and including an agglomerating agent having binding properties, said particles of dental polishing agent being so agglomerated that said agglomerates retain their visibility and palpability in the toothpaste but are reduced to invisible, impalpable particles when said toothpaste is subjected to toothbrushing, said toothpaste base including a polishing material having a refractive index substantially the same as said translucent or transparent toothpaste vehicle in order to maintain visual clarity so as to form a clear gel, the total amount of dental polishing agent and polishing material in said toothpaste being at least 5 percent by weight, said agglomerates being visible both on the surface and in the interior of said clear gel, giving a positive three dimensional sparkling appearance due to the unique light reflectance effects, said agglomerates being inherently white or, when colored, containing about 1 to 10% by weight of water insoluble dye, pigment or lake, said clear gel vehicle having a color different from, or contrasting with, said agglomerates, said gel vehicle containing water and having a total liquid content which is about 20 to 89.5% by weight of the toothpaste.

2. A toothpaste as in claim 1 in which said gel is red and said agglomerates are white.

3. A toothpaste as in claim 1 in which said gel is blue and said agglomerates are white.

4. A toothpaste according to claim 1 wherein said particles of dental polishing agent are selected from the group consisting of insoluble phosphate salts, calcium carbonate, magnesium carbonate, hydrated alumina, silica, zirconium silicate, aluminum silicate, calcined aluminum silicate and polymethyl methacrylate.

5. A toothpaste according to claim 1 wherein said toothpaste base includes a siliceous polishing material.

6. A toothpaste according to claim 1 wherein said polishing material has a refractive index between 1.44 and 1.46.

7. A toothpaste according to claim 6 wherein said toothpaste base contains a silica xerogel polishing material.

8. A toothpaste according to claim 1 wherein said gel base includes a minor amount up to about 10 percent by weight of said agglomerates dispersed therein effective to form a speckled toothpaste.

9. A toothpaste according to claim 8 wherein said gel base further includes between 5 and 20 percent by weight of said polishing material.

10. A toothpaste according to claim 1 wherein said agglomerates have a mean particle size from about 200 and 500 microns.

11. A speckled toothpaste comprising
 a. a transparent or translucent clear gel vehicle having a refractive index between 1.4 and 1.5,
 b. said gel vehicle including between 5 and 20 percent by weight of a siliceous polishing material having a refractive index between 1.4 and 1.5, and
 c. between 1 and 10 percent by weight of agglomerates of impalpable dental polishing agent particles,
 d. said agglomerates including an agglomerating agent having binding or lubricating properties,
 e. said dental polishing agent particles comprising a major amount of said agglomerates,
 F. said combination of polishing materials in the vehicle and the agglomerates being effective in cleansing and polishing power during toothbrushing,
 g. said agglomerates being substantially stable and insoluble in said gel vehicle and being so agglomerated that they retain their visibility and palpability in the toothpaste but are reduced to invisible impalpable particles when the toothpaste is subjected to toothbrushing,
 h. said agglomerates being visible both on the surface and on the interior of said clear gel, giving a positive three dimensional sparkling appearance due to the unique light reflectance effects, said agglomerates being inherently white, or when colored, containing about 1 to 10% by weight water insoluble dye, pigment or lake, said clear gel vehicle having a color different from, or contrasting with, said agglomerates, said gel vehicle containing water and having a total liquid content which is about 20 to 89.5% by weight of the toothpaste, the refractive index of said siliceous polishing material being about the same as that of said gel vehicle in order to maintain visual clarity.

12. A toothpaste as in claim 11 in which said gel is red and said agglomerates are white.

13. A toothpaste as in claim 11 in which said gel is blue and said agglomerates are white.

* * * * *